United States Patent [19]
Fell et al.

[11] Patent Number: 5,850,707
[45] Date of Patent: Dec. 22, 1998

[54] INSECT BAIT

[75] Inventors: Richard D. Fell, Blacksburg, Va.;
Colleen A. Cannon, Berlin, Germany

[73] Assignee: Virginia Tech Intellectual Properties, Inc., Blacksburg, Va.

[21] Appl. No.: 845,366

[22] Filed: Apr. 24, 1997

Related U.S. Application Data

[63] Continuation of Ser. No. 359,694, Dec. 20, 1994, abandoned, which is a continuation-in-part of Ser. No. 69,584, Jun. 1, 1993, abandoned.

[51] Int. Cl.$^6$ ........................................... A01N 63/00
[52] U.S. Cl. ................................ 43/131; 43/114; 424/405
[58] Field of Search ............................. 43/131, 114

[56] References Cited

U.S. PATENT DOCUMENTS

| | | | |
|---|---|---|---|
| 4,160,824 | 7/1979 | Inazuka et al. | 424/84 |
| 4,245,420 | 1/1981 | Carr | 43/42.06 |
| 4,273,571 | 6/1981 | Berg et al. | 71/79 |
| 4,704,286 | 11/1987 | Rittschof et al. | 426/1 |
| 4,855,133 | 8/1989 | Kamei et al. | 424/84 |
| 4,874,611 | 10/1989 | Wilson | 424/492 |
| 4,988,510 | 1/1991 | Brenner | 424/409 |
| 4,988,511 | 1/1991 | Demetre | 424/409 |
| 4,992,268 | 2/1991 | Landolt et al. | 424/77 |
| 4,996,053 | 2/1991 | Hatcher | 424/405 |
| 5,096,710 | 3/1992 | Minagawa | 424/409 |
| 5,140,017 | 8/1992 | Pickford | 424/405 |
| 5,177,107 | 1/1993 | Meen | 424/84 |
| 5,238,681 | 8/1993 | Chang et al. | 424/405 |
| 5,418,164 | 5/1995 | Andersch et al. | 435/254.1 |

FOREIGN PATENT DOCUMENTS

| | | | |
|---|---|---|---|
| 0092357 | 6/1983 | Japan | 43/131 |
| 2018593 | 10/1979 | United Kingdom | 424/409 |

*Primary Examiner*—Joseph J. Hail, III
*Assistant Examiner*—Anthony Ojini
*Attorney, Agent, or Firm*—Whitham, Curtis & Whitham

[57] ABSTRACT

An insect bait specifically formulated for the biology, feeding behavior and food preferences of carpenter ants preferably includes the following ingredients: sucrose and/or fructose sugars; alkali or alkaline earth salts such as sodium chloride, potassium chloride, magnesium chloride, and calcium chloride; urea; and amino acids and/or proteins. Ideally, the bait has a matrix material that has a gelatinous consistency, and, most preferably, the matrix material is agar. Fats and oils are not preferred by carpenter ants; therefore, the use of these materials in the insect bait should be minimized or eliminated. By combining an insecticide with the bait, the material is used to effectively control and eliminate carpenter ant infestations.

11 Claims, 3 Drawing Sheets

INSECT BAIT

CROSS-REFERENCE TO RELATED APPLICATIONS

This patent application is a continuation application of the application having U.S. Ser. No. 08/359,694, filed Dec. 20, 1994, now abandoned, which itself is a continuation-in-part application of the application having U.S. Ser. No. 08/069,584, filed Jun. 1, 1993, now abandoned, and the complete contents of both applications are herein incorporated by reference.

BACKGROUND OF THE INVENTION

1. Field of the Invention

The invention is generally related to insect bait materials and, more particularly, to an insect bait which has constituents specifically chosen and proportioned to enhance the foraging activity of carpenter ants.

2. Description of the Prior Art

The carpenter ant, Camponotus pennsylvanicus, is a wood-infesting insect and common household pest. They are usually considered a nuisance pest, but can cause serious damage to structural wood and timber. Once established in a house, carpenter ants are very difficult to control. Homeowners frequently undertake control efforts themselves by spraying a variety of commercially available insecticides in areas where foragers are observed. Professional pest control operators may also be contacted and the typical treatment procedure used by these professionals involves the application of insecticidal dusts or sprays to a nest in situ, if it can be located. Effective control is hindered by difficulties in nest location, and by the fact that mature carpenter ant colonies often have multiple nests, utilizing both indoor and outdoor sites. When inspections fail to locate nests, insecticides are usually applied to a number of different areas in and around a house. However, this type of practice is inefficient and is rarely effective.

A better and safer alternative to eradicating carpenter ants and other insects in the home involves the use of insecticidal baits. In order to be effective, a bait must be targeted to the feeding preferences of the insect to be eradicated. Baits have the advantage that they can be placed in areas where workers forage so that they can be consumed and transported back to the nest, thus eliminating the need for nest location. Currently, no baits specific for carpenter ants are commercially available due to a lack of knowledge of basic biology, feeding behavior, and food preferences that is required to develop an effective carpenter ant bait material.

U.S. Pat. No. 3,220,921 to Greenbaum et al. discloses the used of an insecticide identified as hexachlorocyclopentadiene for use in ant baits. The Greenbaum et al. reference does not provide any indication as to what kinds of constituents and proportions of those constituents would be attractive to carpenter ants. Rather, Greenbaum et al. merely lists a number of different attractant materials. Many of the materials identified in Greenbaum et al. are not attractive to carpenter ants. In order for a trap to be effective, it must first have a bait that attracts the insects to be eradicated.

U.S. Pat. No. 3,962,461 to Brown, Jr. et al. discloses a honey bait which included a mirex insecticide. The bait in Brown is a liquid. Thus, special procedures are required for the incorporation of the non-water soluble insecticide into the bait. Liquid baits have many drawbacks. For example, a liquid bait must be positioned out of traffic areas since it is subject to spillage and may cause discoloration of floors, rugs, etc. In addition, liquid baits evaporate over time, and the evaporation process causes the dissolved materials to become more concentrated over time. The physical change in the bait which occurs via evaporation is likely to alter the attractive performance of the bait.

U.S. Pat. No. 4,921,696 to Vander Meer et al. discloses a bait material for eradicating fire ants which relies on edible oils as the attractant.

U.S. Pat. No. 4,823,506 to Demarest et al. discloses an insect bait which incudes an insect pheromone.

U.S. Pat. No. 4,988,510 to Brenner et al. discloses an insect bait for cockroaches which utilizes a gel matrix material. The attractant used is corn distiller's dried grains with solubles (C-DDGS). A humectant is used to keep the gel matrix fresh until use.

U.S. Pat. No. 5,096,710 to Minagawa et al. discloses a bait which includes chemicals designed to restrict the proper development of certain insects (e.g., chitin synthesis inhibitors, etc.). The Minagawa et al. bait is provided in tablet form. The Minagawa et al. bait also includes a plant oil as an essential ingredient.

U.S. Pat. No. 5,177,107 to Meer et al. discloses the use of certain fluorocarbon compounds as toxicants for ants.

U.S. Pat. No. 4,988,511 to Demetre discloses an insecticidal paste including powdered boric acid that is designed to harden onto a surface. The paste includes sugars, milk solids, and butter fat.

U.S. Pat. No. 4,996,053 to Hatcher discloses a bait for controlling darkling beetles, hide beetles, and lesser metal worms. The bait includes edible oils including corn and soy oils.

U.S. Pat. No. 4,874,611 to Wilson et al. discloses a microencapsulated ant bait which includes a soybean extract core, an insecticide, and a gelatin shell which includes soy protein as the attractant.

U.S. Pat. No. 4,245,420 to Carr discloses a bait designed for attracting fish. The Carr bait includes a gelatin matrix material which slowly releases the attractant to the water environment.

British Patent GB 2,018,593 to Hurt discloses insect control systems that utilize polymeric carriers such as polyvinylchloride (PVC), polyurethanes, and the like.

None of the prior art references provide a bait formulation which considers the biology, feeding behavior, and food preferences of carpenter ants. In order to successfully eradicate any particular insect, the bait must include materials that will be attractive for the species to be eradicated.

SUMMARY OF THE INVENTION

It is an object of this invention to provide an insect bait material which is specifically designed to attract and eradicate carpenter ants.

It is another object of this invention to provide an insect bait material which utilizes specific sugar constituents in combination with alkali and alkaline earth salts such as NaCl, KCl, $CaCl_2$, and $MgCl_2$.

It is another object of this invention to provide an insect bait which is devoid of saturated and unsaturated fats and oils.

It is another object of this invention to provide an insect bait which utilizes specific sugar constituents in combination with urea.

It is another object of this invention to provide an insect bait which utilizes specific sugars in combination with proteins and certain amino acids.

It is another object of this invention to provide an insect bait which utilizes agar as a matrix material.

According to the invention, the biology, feeding behavior and food preferences of carpenter ants have been investigated and bait materials specific for attracting carpenter ants have been developed. It has been observed that carpenter ants prefer sucrose and fructose to other sugars, and that sucrose and fructose are effective separately or together at low concentrations ranging from 5–40%, and most preferably 10–30%. The consumption rate of a bait material by carpenter ants can also be enhanced significantly by combining either urea or alkali and alkaline earth salts, such as NaCl, KCl, $MgCl_2$, and $CaCl_2$, in the bait material with sucrose and/or fructose sugars. In addition, selection of agar as the matrix material can also enhance the attractiveness of the bait material. Proteins and amino acids are preferred as nutrient source by carpenter ants, and saturated and unsaturated fats and oils are not preferred. Subsequent studies have suggested that the insect bait may be useful as an attractant for several other insect species.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
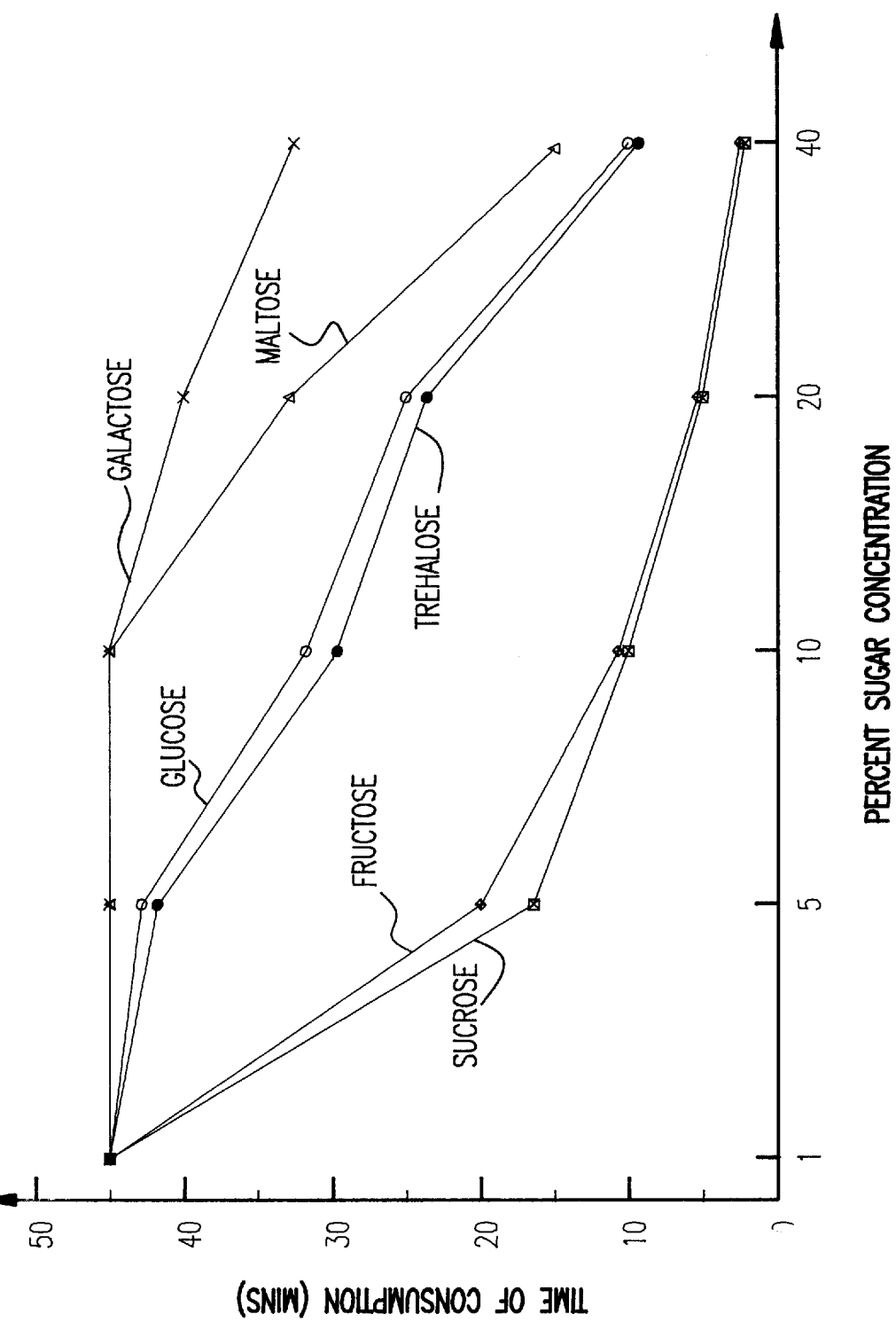
FIG. 1 is a graph showing the consumption rate of different sugars at different concentrations by carpenter ants.

FIG. 1 shows the results of a comparative test where the rate of consumption of different sugars offered to a nest of carpenter ants was monitored. In the tests, solutions of a specified sugar were positioned outside a carpenter ant nest and the time for the carpenter ants to the remove 0.5 mls of the solution was determined. The concentration of the sugar in the solutions ranged from 1% to 40%, and, for each specific sugar constituent, the consumption rate for 1%, 5%, 10%, 20%, and 40% sugar solutions was determined. FIG. 1 shows that more concentrated sugar solutions were generally depleted faster than less concentrated solutions for all the sugars tested; however, it should be understood that sugars are phagostimulants and will have a deterrent effect at too high a concentration.

Most notably, FIG. 1 shows that the rate of consumption of sucrose and fructose was considerably faster than for trehalose, glucose, maltose and galactose, at all concentration levels between 5% and 40% by weight. In addition, FIG. 1 shows that sucrose and fructose sugars were able to provide an attraction to carpenter ants at low concentrations. Specifically, 5% solutions of each sugar were able to provide a significant attraction to carpenter ants as demonstrated by the rate of consumption data. Although not indicated on FIG. 1, it has been determined that the perception threshold for sucrose by carpenter ants is very low (less than 2.5% w/w). The rate of consumption for sucrose and fructose begins to level off for solutions having between 20% and 40% concentration. Thus, having higher concentrations than 40% of sucrose or fructose in a bait will not provide much attraction and consumption benefit to the bait, if any, and may present a deterrent because of factors such as receptor adaptation to the sugars. Hence, an ideal bait for carpenter ants should preferably include 5–40% by weight of sucrose and/or fructose, and most preferably 5–20% or 5–30% by weight of sucrose and/or fructose. Sucrose and fructose can be used in combination in a bait for carpenter ants and will provide a suitable attraction. As discussed above, the effects on attraction and consumption for a combination of sucrose and fructose will begin to level off at a total concentration between 20% and 40%. Thus, suitable baits may include, for example, 1–39% of each of sucrose, fructose, or combinations thereof.

Figure 2:
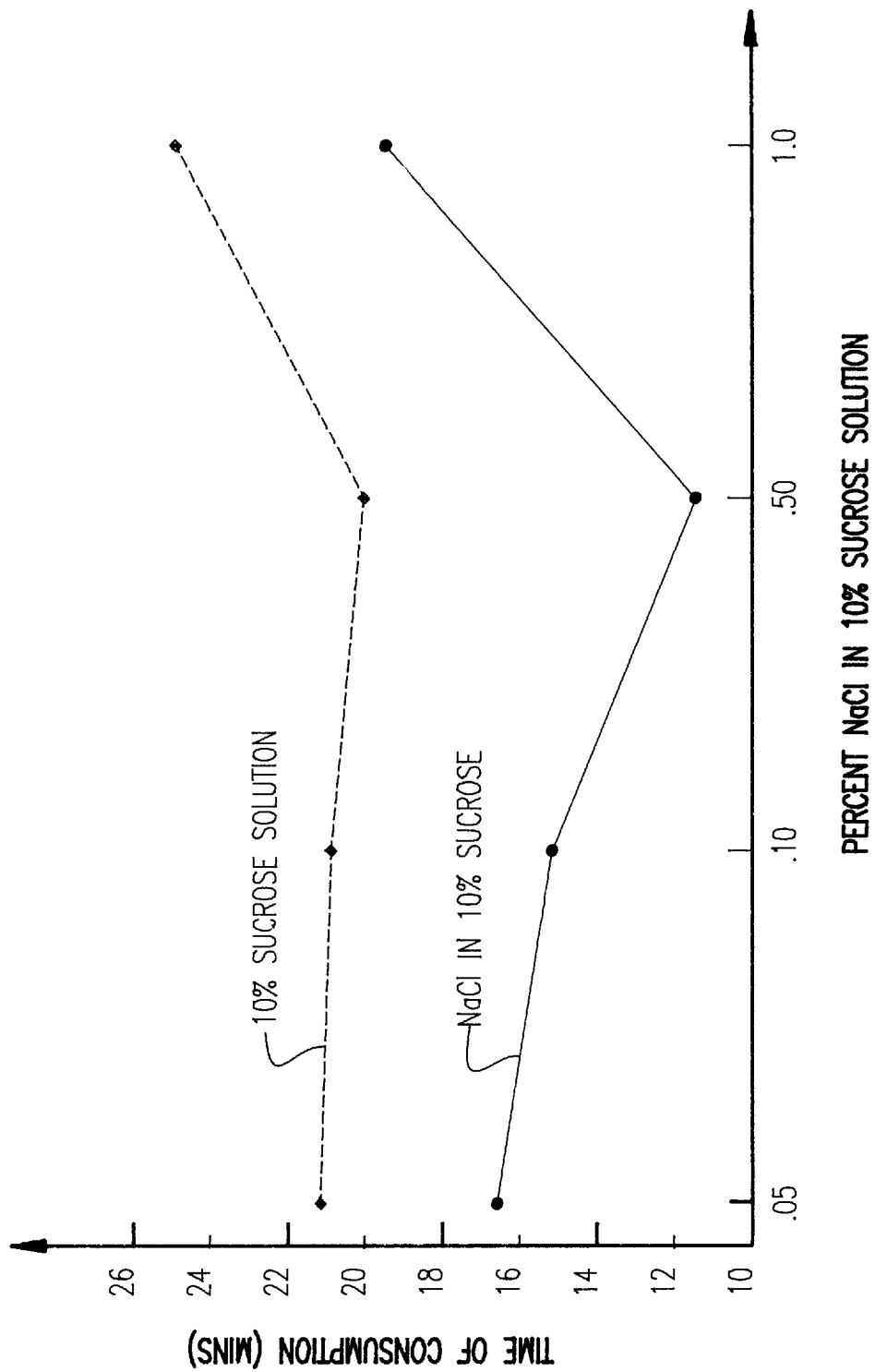
FIG. 2 is a graph showing the relative rate of consumption of a 10% sucrose solution and a 10% sucrose solution plus 10% NaCl.

FIG. 2 shows results for a similar consumption rate test as that described above in conjunction with FIG. 1. Specifically, the consumption rate of a 10% sucrose solution control and a 10% sucrose solution with small quantities of NaCl was determined. The overall rates of consumption differ from those in FIG. 1, but these differences were due, at least in part, to differences in colonly condition (different test colonies) and different temperatures at the time the tests were run. The addition of salt increased the consumption rates of sucrose solutions from 20% to almost 50%. The highest consumption rates were observed at a salt concentration of 0.5%. Consumption rates for sucrose did not change significantly during the test period, although a decrease in consumption of both solutions was noted at the highest salt concentration (1.0%). This decrease reflects a drop in forager numbers and forager recruitment. FIG. 2 shows that including 0.05% to 0.5% NaCl significantly improves the rate of consumption of the sugar solution. Some similar tests also have been run with potassium chloride and increased consumption rates were observed with this salt, although the phagostimulant effects were not as strong as with NaCl. Other alkali and alkaline earth salts such as calcium chloride and magnesium chloride can be expected to have similar results.

In view of the above, including a salt in the carpenter ant bait material should provide for enhanced attraction of the bait, and, preferably, the salt will constitute 0.1%–1% by weight of the bait. The results in FIG. 2 suggest a decrease in feeding as the salt concentration approaches 1% by weight.

Figure 3:
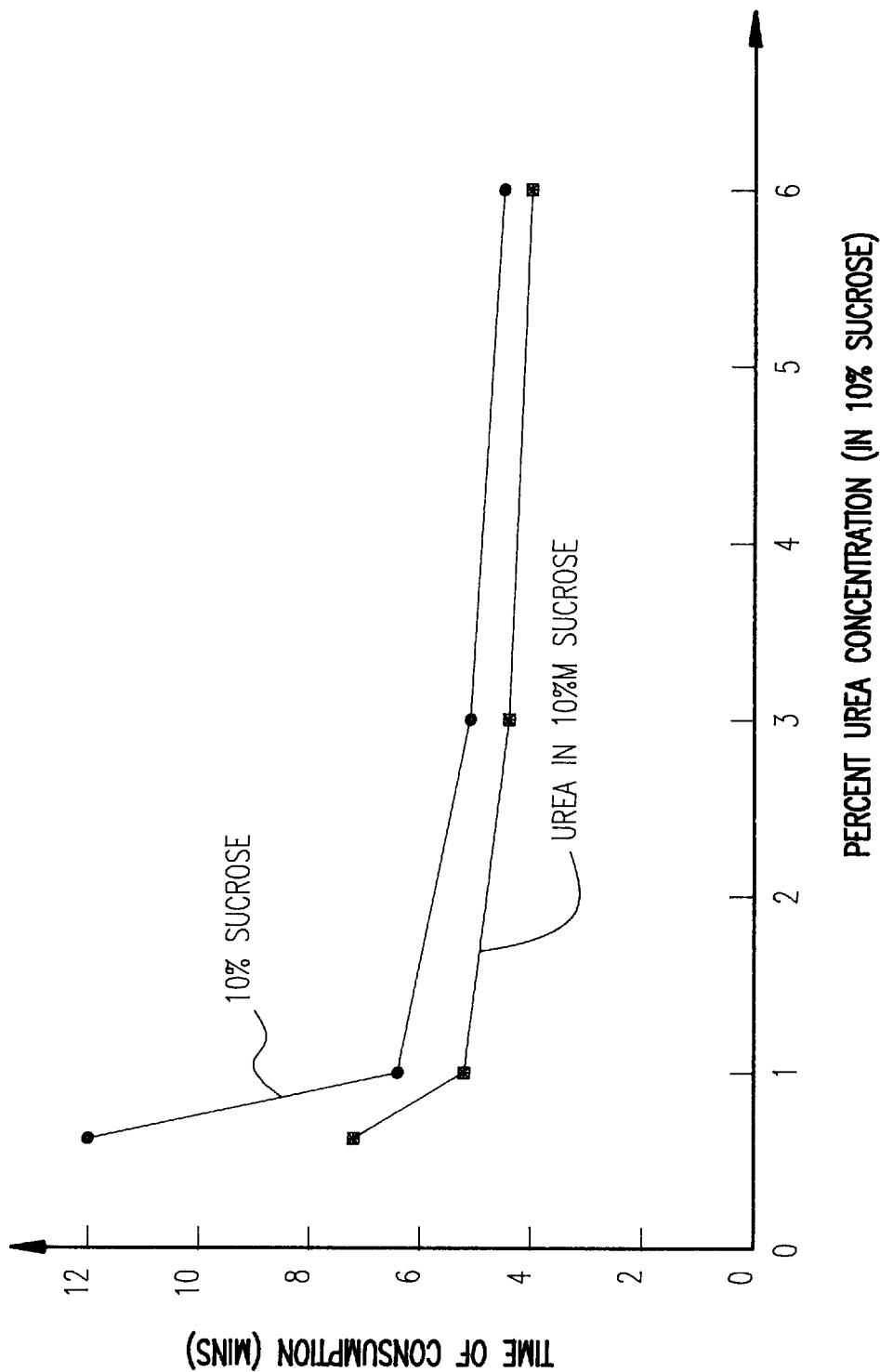
FIG. 3 is a graph showing the relative rate of consumption of a 10% sucrose solution and a 10% sucrose solution plus 10% urea.

FIG. 3 shows results for a similar consumption rate test as that described above in conjunction with FIG. 1. Specifically, the consumption rate of a 10% sucrose solution control and a 10% sucrose solution with varying concentrations of urea ranging from 0.5% to 6% were determined. FIG. 3 shows the addition of urea also increased the consumption rate of a standard 10% sucrose solution. Significant effects were noted with a urea concentration as low as 0.5%, wherein the consumption rate was increased by approximately 30%. The increase in consumption rates for the sugar controls was due to increased recruitment with the presentation of the two food sources. Forager numbers increased at both test solutions, but collection of urea occured at higher rates. Urea concentrations above 3% did not appear to lead to continued increases in consumption.

In view of FIG. 3 showing that including urea in combination with the sucrose improves the rate of consumption of the solution, urea would be a preferable component of an insect bait. Preferably, in a bait material, the urea would constitute 0.5%–4.0% by weight of the bait.

Consumption tests similar to that described in conjunction with FIG. 1 were conducted with solutions containing amino acids and proteins. It was determined that proteins, and particularly protein hydrolysates such as Hy-Case (an acid digest of casein available from Sigma Chemical), Biosate (a bacteriological peptone that is composed of plant and animal protein hydrolysates—yeast autolysate and pancreatic casein digest, available from the Baltimore Biological Laboratory), and Gelysate (a pancreatic hydrolysate of gelatin available from the Baltimore Biological Laboratory), all of which are water soluble protein mixtures, were attractive to carpenter ants at concentrations as low as 1% wt/wt. The rate of consumption of the hydrolysate solution leveled off between 10–40%; therefore, including higher concentrations of a water soluble protein hydrolysate than 40% in a bait material is not beneficial. Preferably, a bait will include 1–20% of a water soluble protein hydrolysate. It was also determined that certain, water soluble, amino acids, and particularly leucine, valine, and proline were attractive to carpenter ants at concentrations as low as 0.5% wt/wt. In contrast, solutions containing aspartic acid and glutaric acid did not demonstrate any attractive effect on carpenter ants. Preferably, a bait material will include 0.5–20% of amino acids, and particularly leucine, valine, and proline. In addition, amino acids may be used in a bait in combination with proteins.

In a series of "choice" tests, carpenter ant nests were simultaneously offered baits with sugars and carbohydrates, baits with fats and oils, and baits with proteins, where all of the baits were placed side-by-side. The baits included a gelatin matrix material with the proteins, fats and oils, or sugars and carbohydrates dispersed within the matrix. The carpenter ants routinely selected the baits with proteins and the baits with sugars and carbohydrates. Baits with fats and oils, including both saturated and unsaturated fats and oils from both animal and plant sources, were never accepted by carpenter ants during choice tests. Therefore, carpenter ant baits preferably should not include any fats and oils and, if included, the amount should be minimized so that the bait will not present a deterrent to the carpenter ants. Thus, for example, if flour is to be included in the bait material, it would be preferable to use de-fatted flour. An interesting result from the "choice" tests was that carpenter ants routinely removed more nutrient from the protein baits than from the sugar baits.

In order to facilitate long term usage, baits should generally be solid rather than liquid. However, carpenter ants typically only ingest liquids. Thus, it has been determined that providing the bait with a matrix that is gelatinous in character is preferred for carpenter ants to meet both the shelf-life and other requirements of a bait material product, and the "liquid-food" requirements of the carpenter ant. The preferred matrix material is agar; however, other useful matrices include gelatin, carrageenan, starch, acacia, guar gum, pectin, starch, proteins, collagen, and synthetic polymers such as polyvinylpyrrolidone, and these constituents can be used alone or in combination to make the matrix material. Preferably, the matrix material comprises 0.5% to 4.0% by weight of the bait material.

Consumption tests similar to those described in conjunction with FIG. 1 have shown that agar is more attractive to carpenter ants than gelatin. When the agar baits and gelatin baits were offered to the same carpenter ant nests, the carpenter ants consumed the agar baits, on average, at a greater rate than the gelatin baits. Therefore, it is preferable to formulate carpenter ant baits with an agar matrix material.

The ideal insecticide for use in the bait would be one that can be picked up by the forager and carried back to the nest to be passed around to other carpenter ants. Contact insecticides would not generally be suitable since the bait material would then only be useful for killing foragers. Sulfimide, hydramethylnon, and abamectin are examples of suitable insecticides. Preferably, the insecticide constitutes 0.01–10% by weight of the bait.

While the above studies have been conducted with carpenter ants (Camponotus species), it has been noted that the baits are effective attractants for a wide variety of other insects, particularly insects with chewing mouth parts and those with sponging and lapping mouth parts. The insect baits of this invention are especially effective for the control of ants, Family Formicidae, and may be used for the control of ants such as the southern fire ant, *Solenopsis xyloni*, leaf cutting ants, *Acromyrmex versicolor*, Argentine ants, *Iridomyrmex humilis*, cornfield ants, *Lasius alienus*, pavement ants, *Tetramorium caespitum*, larger yellow ants, *Acanothomyops interjectus*, thief ants, *Solenopsis molesta*, and the red and black imported fire ants, *Solenopsis invicta* and *Solenopsis saevissma richteri*, respectively. These ants are serious economic pests which have been known to attack human beings, livestock, and agronomic crops; therefore, it is highly desirable to control them. Other ants that can be controlled are nuisance pests such as Pharaoh ants, *Monomorium pharaohnis*; oderous house ants, *Tapinoma sessile*; and acrobat ants, *Crematogaster cerasi*.

A simple procedure for formulating an agar based bait, provided herein for exemplary purposes only, would be to add 6 grams of agar to 500 ml of distilled water, bringing the agar/water mixture to boil, adding the attractant material to the agar/water mixture when it is fluidized (e.g., sucrose and/or fructose and/or proteins and/or amino acids and/or alkali or alkaline earth salts and/or urea and/or carbohydrates and/or insecticide), and then cooling the mixture. The mixture may be molded to form a desired bait shape. It should be understood that the amounts of constituents added to the agar/water mixture can be varied considerably within the practice of this invention, and that the amounts of agar and water employed will vary depending on the bait being formulated.

While the invention has been described in terms of its preferred embodiments, those skilled in the art will recognize that the invention can be practiced with modification within the spirit and scope of the appended claims.

We claim:

1. An insect bait, comprising:

a gelatinized matrix material;

a sugar or combination of sugars dispersed in said matrix material; and casein hydrolysate dispersed in said matrix material, said casein hydrolysate constituting 1–20% by weight.

2. The insect bait recited in claim 1 wherein said matrix material is selected from the group consisting of agar gelatin, carrageenan, starch, acacia, agarose, guar gum, pectin, collagen and polyvinylpyrrolidone.

3. The insect bait recited in claim 2 wherein said matrix material is selected from the group consisting of agar and carageenan.

4. The insect bait recited in claim 1 wherein said sugar or combination of sugars comprise 5–40% by weight.

5. The insect bait recited in claim 1 further comprising a foraging enchancer selected from the group consisting of amino acids and proteins.

6. The insect bait recited in claim 1 being devoid of fats and oils.

7. The insect bait recited in claim 1 further comprising an insecticide.

8. The insect bait recited in claim 7 wherein said insecticide has delayed killing activity.

9. The insect bait of claim 1 wherein sugar is selected from the group consisting of sucrose and fructose.

10. The insect of claim 1 further comprising an alkali or alkaline earth salt selected from the group consisting of sodium, chloride, potassium chloride, calcium chloride, and magnesium chloride.

11. The insect bait recited in claim 10 wherein said alkali or alkaline earth salt is sodium chloride.

* * * * *